United States Patent [19]

Sorrentino et al.

[11] 4,007,261
[45] Feb. 8, 1977

[54] PEARLESCENT HAIR CONDITIONER

[75] Inventors: Ralph P. Sorrentino, Old Bridge;
Burton M. Like, East Brunswick,
both of N.J.

[73] Assignee: Millmaster Onyx Corporation, New York, N.Y.

[22] Filed: Aug. 23, 1972

[21] Appl. No.: 283,089

[52] U.S. Cl. .................................................. 424/70
[51] Int. Cl.² .......................................... A61K 7/06
[58] Field of Search .................... 424/70; 8/10.1

[56] References Cited

UNITED STATES PATENTS

| | | | |
|---|---|---|---|
| 3,098,794 | 7/1963 | Dohr et al. | 8/10.1 |
| 3,206,512 | 9/1965 | Koebner et al. | 424/70 X |
| 3,449,430 | 6/1969 | Dohr et al. | 424/70 X |
| 3,494,962 | 2/1970 | Miller, Jr. et al. | 424/70 X |
| 3,496,110 | 2/1970 | Shumway et al. | 424/70 X |
| 3,577,528 | 5/1971 | McDonough et al. | 424/329 X |
| 3,708,426 | 1/1973 | Schrader | 424/70 X |

*Primary Examiner*—Dale R. Ore
*Attorney, Agent, or Firm*—Arthur A. Jacobs

[57] ABSTRACT

Pearlescent hair conditioning compositions comprising aqueous emulsions or dispersions of alkyl dimethylamine oxides having from 16-22 carbon atoms in the alkyl chain.

4 Claims, No Drawings

PEARLESCENT HAIR CONDITIONER

This invention relates to conditioning agents for conditioning hair, and especially human hair; and it more particularly relates to conditioning agents which provide a pearlescent effect without the use of additives.

It has, heretofore, been common practice in the cosmetic field to add certain auxiliary materials to hair conditioning agents in order to provide a pearlescent effect which is considered highly desirable. Such additives have generally included such substances as cetyl or stearyl alcohols, glycol higher fatty acidesters, or amides, such as monoisopropanolamines; as well as others, which serve no purpose other than to provide a pearlescent appearance in an emulsion or dispersion.

In accordance with the present invention, the conditioning agent itself provides the desired pearlescent effect, thereby eliminating the need for other additives.

The purpose of hair-conditioning agents is to soften the hair, to help disperse static electric charges, and to otherwise aid in its manageability. They are usually in the form of aqueous emulsions or dispersions, more or less creamy in nature, and are often referred to in the trade as "creme rinses". They are ordinarily applied to the hair subsequent to a preliminary washing or shampooing and rinsing.

The hair-conditioning agents of the present invention consist essentially of aqueous emulsions or dispersions of alkyldimethylamine oxides having from 16 to 22 carbons in the alkyl chain. The alkyl is preferably straight chain, although a small amount of branching may be present, but such branching is preferably kept to a minimum since it tends to reduce pearlescence.

In general, the aqueous dilution (emulsion or dispersion) should be in the range of between about 1:8 and 1:48, with other optional ingredients such as alcohols, acids, coloring agents, preservatives, perfumes, etc., added in desired proportions in accordance with the particular area of use.

The amine oxides of the present invention may be prepared by methods well known to the art, such as by reaction in aqueous or other suitable solution with a peroxide, such as hydrogen peroxide, or with ozone. Hydrogen peroxide is preferred, however.

Creme rinse formulations, embodying the present invention, were prepared as follows, it being understood that the concentrations may be varied as desired within the above limits, and it being also understood that the products are prepared at, or adjusted to, a pH below 7.0, and preferably between 5.0 and 6.0:

EXAMPLE 1

Example 1

| Component | Parts by Weight |
|---|---|
| "Ammonyx SO" (Onyx Chemical Co.) (25% active stearyl dimethyl amine oxide) | 7.5 |
| Water | 92.27 |
| 1:1 dilution in water of 36% HCl | 0.23 |
| Color, Perfume, Preservative | as desired |

The "Ammonyx SO" and the water were heated together with agitation until thoroughly mixed. The hydrochloric acid was added in small increments until the pH was adjusted to about 5.5.

The mixing was then continued for about 15 minutes at the same temperature.

The mixture was cooled gradually, with moderate agitation, to room temperature, avoiding localized cooling. Meanwhile, the coloring matter, perfume and preservative were added.

The product was a creme rinse of excellent appearance and pearlescence.

EXAMPLE 2

In the same manner, and at the same active content, a pearlescent creme rinse was prepared substituting "Ammonyx CO" (Onyx Chemical Co.), a cetyl dimethyl amine oxide of 30% active content.

EXAMPLE 3

Similarly to Example 1, a pearlescent creme rinse of excellent quality was prepared using "Kemamine" (Humko), a mixture of $C_{20}$ and $C_{22}$ dimethyl amines which had been converted to the corresponding amine oxides at about 20% active content in aqueous solution.

EXAMPLE 4

By the same procedure, "Ammonyx MO" (Onyx Chemical Co.), myristyl dimethyl amine oxide, 30% active, which was utilized in the same manner as in Example 1, produced a clear liquid, but not noticeably pearlescent.

EXAMPLE 5

A creme rinse of traditional type was prepared for purposes of comparison, using instead of the $C_{16}$–$C_{22}$ dimethyl amine oxides, "Ammonyx 4" (Onyx Chemical Co.), a 25% active stearyl dimethyl benzyl ammonium chloride. This product was found to give no pearlescent effect until a quantity of cetyl alcohol and potassium chloride was added. This formulation was as follows:

| Component | Parts by Weight |
|---|---|
| "Ammonyx 4" | 7.50 |
| Cetyl alcohol | 0.30 |
| Water (1) | 81.45 |
| KCl | 0.75 |
| Water (2) | 10.00 |
| Perfume, Color, Preservative | as desired |

The "Ammonyx 4", cetyl alcohol and water (1) were heated to 60°–70° C with agitation until uniform. The KCl and water (2) were then gradually added, maintaining the temperature for at least 15 minutes. The mixture, still under agitation, was cooled to 40°–50° C, and the perfume, color and preservative were added. At the set point, about 28°–30° C, the mixing was slowed down to prevent localized cooling. The product falls naturally in the desired pH range.

Alkyl dimethyl amine oxides of less than $C_{16}$ alkyl thus did not yield pearlescent creme rinses without additives, while $C_{16}$–$C_{22}$ alkyls by themselves, gave very satisfactory products.

In addition to the pearlescent effect, a shampoo tress test was applied to evaluate these products for conditioning effects. The hair used was De Meo - European brown hair in 3.0 gram tresses, and the procedure was as follows; two tresses being treated for each test:

Each tress was wet out in tap water at 105° F. One ml of a shampoo (a 10% active solution of "Maprofix WAC" (Onyx Chemical Co.), a fatty-alcohol sulfate) was applied to the tress, which was then washed for 30 seconds working between thumb and forefinger from top to bottom and the reverse. The shampoo was then rinsed out of the tress for 10 seconds under tap water. The shampooing and rinsing were repeated a second time.

30 ml of the creme rinse formulation was diluted to 240 ml with water. The tress was swirled in this solution for 10 seconds, withdrawn and rinsed under tap water for 10 seconds.

Next the tress was wet-combed and observed, for ease of combing.

The excess water was then squeezed out. One of the tresses was hung straight, the other was curled, and both were air-dried at room temperature. They were then dry-combed and evaluated for ease of combing, "fly-away" (due to static electric charges) and curl retention.

Table I

| Creme Rinse from | Wet Comb | Dry Comb | "Fly-Away" | Curl Retention |
| --- | --- | --- | --- | --- |
| Example 1 ($C_{18}$) | Excellent | Excellent | ½ inch | Good/Excellent |
| Example 2 ($C_{16}$) | Excellent | Good/Excellent | ½ inch to ¾ inch | Good/Excellent |
| Example 3 ($C_{20}, - C_{22}$) | Excellent | Excellent | 1 inch | Good |
| Example 4 ($C_{14}$) | Good/Excellent | Good | 1½ inch | Good |
| Example 5 (Ammonyx 4") | Excellent | Good | 2 inches | Fair |
| None | Poor | Poor-Raspy | 3 inches | Poor |

The above demonstrates that the alkyl dimethyl amine oxides wherein the alkyl has 16 to 22 carbon atoms, unexpectedly are self-opacifying and pearlizing, and, in addition, are superior to those containing lower alkyl chains in conditioning performance.

The application of the above conditioner solutions to human hair tress samples requires "swirling" for 10 seconds for test purposes. It is to be understood, however, that by reason of the larger mass and area of the human scalp and its hair, such a short time may be adequate for proper coverage. It is customary to apply a creme rinse for from one to two minutes, and this period of time is adequate for the purpose. Similarly, the shampooing of a test tress was timed at 30 seconds. This is not intended to limit such shampooing to that period of time, which may be variable from person according to preference, the type of shampooing agent used, and the condition of the hair.

The invention claimed is:

1. A method of simultaneously obtaining pearlescence and conditioning of hair which comprises applying to the hair an aqueous composition consisting essentially of a conditioning agent and water, said conditioning agent being alkyl dimethylamine oxide wherein the alkyl is substantially straight chain and has 16 to 22 carbon atoms and said conditioning agent being applied in an effective amount sufficient to obtain both pearlescence and conditioning of the hair.

2. The method of claim 1 wherein the ratio of conditioning agent to water is between about 1:8 and 1:48 parts by weight.

3. The method of claim 1 wherein the hair is first washed and rinsed prior to application of the aqueous composition.

4. The method of claim 1 wherein the aqueous composition is retained on the hair for from about 1 to 2 minutes, followed by an aqueous rinsing sufficient to remove excess composition from the hair.

* * * * *